United States Patent
Dwarki et al.

(10) Patent No.: US 6,221,646 B1
(45) Date of Patent: *Apr. 24, 2001

(54) MATERIALS AND METHODS FOR SIMPLIFIED AAV PRODUCTION

(75) Inventors: Varavani Dwarki, Alameda; Martha Baillie Ladner, Oakland; Jaime Escobedo, Alamo; Shang-Zhen Zhou, Alameda, all of CA (US)

(73) Assignee: Chiron Corporation, Emeryville, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/127,268

(22) Filed: Jul. 31, 1998

Related U.S. Application Data

(60) Provisional application No. 60/054,371, filed on Jul. 31, 1997.

(51) Int. Cl.[7] .............................. C12N 7/01; C12N 15/00; C12N 7/02
(52) U.S. Cl. .................. 435/235.1; 435/239; 435/320.1; 435/69.1; 536/23.1
(58) Field of Search ................................ 435/235.1, 239, 435/320.1, 69.1; 536/23.1

(56) References Cited

U.S. PATENT DOCUMENTS

| | | | |
|---|---|---|---|
| 5,681,731 | * 10/1997 | Lebkowski et al. | 435/457 |
| 5,945,335 | 8/1999 | Colosi | 435/369 |

FOREIGN PATENT DOCUMENTS

| | | |
|---|---|---|
| WO 94/12649 | 6/1994 | (WO) . |
| WO 96/40240 | 12/1996 | (WO) . |
| WO 97/17458 | 5/1997 | (WO) . |
| WO 99/06562 | 2/1999 | (WO) . |

OTHER PUBLICATIONS

Tamayose et al., Mar. 1, 1996, "A New Strategy for Large–Scale Preparation of High–Titer Recombinant Adeno–Associated Virus Vectors by Using Packaging Cell Lines and Sulfonated Cellulose Column Chromatography" *Human Gene Therapy* 7:507–513.

Xiao et al., Mar. 1998, "Production of High–Titer Recombinant Adeno–Associated Virus Vectors in the Absence of Helper Adenovirus" *Journal of Virology* 72(3):2224–2232.

Matsushita et al., 1998, "Adeno–Associated Virus Vectors can be Efficiently Produced without Helper Virus" *Gene Therapy* 5:938–945.

Ferrari et al., "New Developments in the Generation of Ad–Free, High–Titer rAAV Gene Therapy Vectors" *Nature Medicine* 3(11):1295–1297, Nov. 1997.

Grable et al., "cis and trans Requirements for the Selective Packaging of Adenvirus Type 5 DNA" *Journal of Virology* 66(2):723–731, Feb. 1992.

* cited by examiner

*Primary Examiner*—Ali R. Salimi
(74) *Attorney, Agent, or Firm*—Donald Pochopien; Anne S. Dollard; Robert P. Blackburn

(57) ABSTRACT

The invention provides a method for producing purified replication-defective recombinant AAV virions. The method comprises introducing into a suitable host cell an AAV vector, an AAV helper construct and an adenoplasmid accessory construct into the host cell. The adenoplasmid accessory plasmid is composed adenovirus plasmid DNA unable to be packaged into adenoviral particles because it lacks packaging signal sequence(s) or it contains additional sequences making it too large to package. The host cell is cultured to produce crude rAAV virions and then lysed. The resulting cell lysate is applied to a chromatographic column containing sulfonated cellulose or subjected to cesium chloride equilibrium gradient centrifugation and the purified rAAV virions are recovered.

17 Claims, No Drawings

MATERIALS AND METHODS FOR SIMPLIFIED AAV PRODUCTION

This application is related to provisional application s. n. 60/054,371, filed Jul. 31, 1997, from which priority is claimed under 37 C.F.R. §119 and which is incorporated herein by reference in its entirety.

BACKGROUND

A. Field of the Invention

The present invention is directed to a method for the production of recombinant AAV virions containing a gene of interest. More particularly, the present invention is directed to a method for producing rAAV virions free of wild-type AAV and helper virus. The present invention is useful because it produces a highly pure rAAV virion suitable for evaluation of gene therapy protocols and/or use in gene therapy.

B. Background of the Invention

Adeno-associated virus (AAV) is a non-pathogenic, replication-defective parvovirus that has a biphasic life cycle. In the absence of a helper virus, the AAV genome integrates into the hot cell's genome to establish a latent infection. In the presence of a helper virus, such as adenovirus, herpes simplex virus or vaccinia virus, the AAV genome is rescued from latency and is reproduced to establish a lytic infection. See Muzyczka, *Curr. Topics Microbiol Immunol.* 158 (1992) 97-129; Berns and Linden, *BioEssays* 17 (1995) 237–245. The helper virus is known to provide the functions needed for AAV replication. In the absence of helper virus, AAV stably integrates into human chromosome 19 site specifically. See Kotin, *Proc. Natl. Acad. Sci.* 87 (1990) 2211–15; Samulski, *EMBO J* 10 (1991) 3941–50. The AAV genome consists of a 4.7 kb linear, single-stranded, DNA molecule with 145 bp inverted terminal repeats at each end. The remaining, non-repeated sequences encode for the viral proteins, called rep and cap, involved in virus replication and packaging. The AAV ITRs are the only cis elements required for the viral replication, packaging and integration; the rep and cap functions can be provided in trans. See McLaughlin, *J. Virol.* 62 (1988) 1963–73; Samulski *J. Virol.* 63 (1989) 3822–28.

Recombinant AAV (rAAV) vectors are attractive vehicles for human gene therapy because the vectors do not require AAV coding sequences to be expressed viral coding sequences, the viruses (viral particles) is capable of infecting non-dividing and dividing cells efficiently, it has a broad host range and the virions have high physical stability. See Carter, *Curr. Opin. Biotech* 3 (1992) 533–39; Bachman, *Intervirology* 11 (1979) 248–54. The most widely used method of generating rAAV particles is called the invention/transfection method. This method involves transfection of host cells, typically 293 cells, with AAV vector plasmid (i.e., plasmid carrying the gene of interest bounded by the AAV ITRs) and with helper plasmid (i.e., plasmid providing the AAV helper functions rep and cap but lacking the ITRs) and infection with adenovirus or herpes virus. See McCown, *Brain Res.* 713 (1996) 99–107; McLaughlin, *J. Virol* 62 (1988) 1963–73In this standard method, the helper virus can be separated from AAV vectors by density gradient centrifugation and any residual infectious helper virus inactivated by heat. However, the resulting AAV vector preparations still may contain low levels of infectious helper virus and proteins that may contribute to the immunogenicity of the composition and present a potential hazard for human administration. Also, the helper virus is a pathogenic virus and poses a health risk to laboratory personnel involved in the manufacturing process. Moreover, the large amount of helper virus particles and proteins generated during the infection process makes it difficult to achieve high levels of purity. Heat treatment can inactivate infectious adenovirus, but the treatment leads to a 30–40% drop in the tier of functional rAAV virions and it has been difficult to remove all of the adenoviral proteins, even by multiple rounds of CsCI gradient purifications.

Recently, there have been reports of rAAV production using cell lines providing the necessary helper function for rAAV packaging. See for example, Clark, *Gene Therapy* 3 (1996) 1124–32; Chiorini, *Human Gene Therapy* 6 (1995) 1531–42; Clark, *Gene Therapy* 6 (1995) 132941, Flotte *Gene Therapy* 2 (1995) 29–37 and Tamayose, *Human Gene Therapy* 7 (1995) 507–13. this method likewise leads to the generation of infectious adenovirus or herpes virus, which must be purified away from the rAAV particles. Although rAAV particles can be purified on CsCl gradients, often the final preparations are contaminated with adenovirus. Also, CsCl gradient centrifugation protocol is cumbersome to adapt to large-scale manufacturing.

There are several studies employing adenovirus mutants delineating the role of various regions of adenovirus (helper virus) necessary for AAV production. There is evidence to demonstrate that the adenoviral DNA replication genes, E2b, E3 and several adenoviral late genes are not required for AAV replication. See Laughlin, *J. Virol.* 41 1982) 868–876; Myers, *J. Virol.* 35 (1980) 65–75; Jay, *Proc. Natl. Acad. Sci.* 78 (1981) 2927–31; Carter, *Virology* 126 (1983) 505–16; Ito and Sazuki, *J. Gen. Virol.* 9 (1970) 243–45; Strauss, *J. Virol.* 17 (1975) 140–48; and Janik, *Virology* 168 (1989) 320–29. From these results, it can be predicated that the "accessory" functions that may be necessary to support AAV replication include adenoproteins E2a and E4, as well as VA I RNA. An alternative method of producing rAAV is disclosed in PCT Patent Publication WO 97/17458, published May 15, 1997. In that document, the accessory functions capable of supporting rAAV virion production are provided in the from of one or more vectors containing the adenovirus VA sequence, the adenovirus E4 ORF6 coding region and/or the adenovirus E2a 72 kD coding region. However, upon production of the rAAV virions, numerous adenoviral proteins encoded by the foregoing sequences are produced and must be removed. Moreover, the production of rAAV using the helper vectors described in WO 97/17458 is undesirable because it requires periodic auditing to verify the continued presence and operability of the vectors. Accordingly, there remains a need in the art to provide a system capable of producing commercially significant levels of rAAV virions simply and efficiently.

SUMMARY OF THE INVENTION

The present invention is directed to a method for producing replication-defective AAV virions that avoids the production of live adenovirus, the necessity of monitoring for multiple adenoviral accessory functions, and the need for cumbersome purification protocols. More particularly, the present invention is directed to a method for producing replication-defective recombinant AAV virions substantially free of wild-type AAV and helper adenovirus, comprising:

a. introducing into a suitable host cell (i) an AAV vector that is free of AAV coding sequences and that comprises a heterologous gene operatively positioned between two AAV ITRs, (ii) a replication-defective AAV helper construct having at least one gene encoding an AAV capsid protein, and (iii) an adenoplasmid accessory construct having a full adenoviral genome that either lacks a packaging signal or that contains sufficient additional nucleotides to be rendered unpackagable, to produce a transformed host cell;

b. culturing the transformed host cell to produce replication-defective recombinant AAV virions having the heterologous gene; and c. lysing the cultured host cell to obtain replication-defective recombinant AAV virions substantially free of wild-type AAV and adenovirus particles.

The host cells that are suitable for use in the method of the present invention are mammalian host cells, preferably human host cells.

In another aspect, the invention is directed to a method of producing purified recombinant AAV virions, comprising:

a. introducing into a suitable host cell (i) an AAV vector that is free of AAV coding sequences and that comprises a heterologous gene operatively positioned between two AAV ITRs, (ii) a replication-defective AAV helper construct having at least one gene encoding an AAV capsid protein, and (iii) an adenoplasmid accessory construct having a full adenoviral genome that either lacks packaging signal or that contains sufficient additional nucleotides to be rendered unpackagable, to produce a transformed host cell;

b. culturing the transformed host cell to produce replication-effective recombinant AAV virions having the heterologous gene;

c. lysing the cultured host cell to obtain replication-defective recombinant AAV virions substantially free of wild-type AAV and adenovirus particles;

d. applying the lysate of step (c) to a column comprising sulfonated cellulose; and e. recovering purified replication-defective recombinant AAV virions substantially free of host cell proteins and host cell debris.

Alternatively, the lysate from step (c) is subjected to cesium chloride equilibrium gradient centrifugation, and the purified replication-defective rAAV virions containing the heterologous gene are recovered. The AAV vector, the replication-defective AAV helper construct and the adenoplasmid accessory construct are combined either simultaneously or sequentially.

The advantage of the triple transfection protocol utilized in the methods of the present invention is the significant purity of rAAV preparations after CsCl gradient purification. The Western plot analysis shows that the triple transfection method, while producing equivalent amounts of rAAV particles as the standard transfection/infection protocol, results in much lower adenovirus protein production in both the initial lysates and in the final purified product. This demonstrates the advantage of the triple transfection protocol over the standard prior art transfection/infection protocol, in which there is a significant amplification of adenovirus in the culture and robust adenovirus gene expression. In addition, because the adenoplasmid accessory construct used in the methods the this example lacks a packaging signal, there are no adenovirus particles in the purified material. This protocol also eliminates the health and safety concerns raised by the use of live adenovirus and allows production of rAAV particles in a safe manner. Importantly, the method simplifies the downstream purification process, thereby enabling relatively efficient and economical large-scale manufacturing.

DETAILED DESCRIPTION OF THE INVENTION

In its first aspect, the present invention is directed to a method for producing replication-defective recombinant AAV virions substantially free of wild-type AAV and helper adenovirus, comprising:

a. introducing into a suitable host cell (i) an AAV vector that is free of AAV coding sequences and that comprises a heterologous gene operatively positioned between two AAV ITRs, (ii) a replication defective AAV helper construct having at least one gene encoding an AAV capsid protein, and (iii) an adenoplasmid accessory construct having a full adenoviral genome that either lacks a packaging signal or that contains sufficient additional nucleotides to be rendered unpackagable, to produce a transformed host cell;

b. culturing the transformed host cell to produce replication-defective recombinant AAV virions having the heterologous gene; and c. lysing the cultured host cell to obtain replication-defective recombinant AAV virions substantially free of wild-type AAV and adenovirus particles.

It is within the scope of the present invention that the above described method further comprise the steps of:

d. applying the lysate of step (c) to a column comprising sulfonated cellulose; and e. recovering purified replication-defective recombinant AAV virions substantially free of host cell proteins and host cell debris.

The host cells that are suitable for use in the method of the present invention are mammalian host cells, preferably human host cells.

The AAV vector, replication-defective AAV helper construct and adenoplasmid accessory construct of step (a) of the method of the present invention are prepared using conventional methods of virology, molecular biology, microbiology and recombinant DNA techniques. Such techniques are well known and explained fully in the literature, including, for example, in Sambrook, Molecular Cloning: A Laboratory Manual (Current Ed.); DNA Cloning: A Practical Approach (D. Glover, ed.); Oligonucleotide Synthesis (Current Ed., N. Gait, ed.); Nucleic Acid Hybridization (Current Ed., B. Hames and S. Higgins, eds.); Transcription and Translation (Current Ed., B. Hames and S. Higgins, eds.); CRC Handbook of Parvoviruses (P. Tijessen, ed.); Fundamental Virology, 2d Edition (B. N. Fields and D. M. Knipe, eds.); Current Protocols in Human Genetics, Vol. 1 (N. Dracopoli, ed.). These publications and all other publications referenced throughout this specification are expressly incorporated herein by reference.

Gene transfer, gene therapy or gene delivery refer to methods, techniques or systems for reliably inserting into a host cell a heterologous or a foreign DNA or a DNA not normally expressed. The resultant insertion can be by integration of transferred genetic material into the host cell genomic DNA, by extrachromosomal replication and expression of transferred replicons or in a non-integrated manner.

Vector means any genetic element that is capable of replication when associated with the proper control elements and that can transfer DNA or RNA sequences between cells. Examples include plasmids, phages, transposons, cosmids, chromosomes, viruses, and virions and include cloning and expression vehicles and viral vectors.

The replication-defective AAV virions produced by the method of the present invention comprise a gene (DNA) encoding a therapeutic protein operably positioned between a pair of adeno-associated virus inverted terminal repeats ("AAV ITRs"). AAV ITRs are art-recognized regions found at each end of the AAV genome that function together in cis as recognition signals for DNA replication and for packaging the AAV vector into an AAV coat. The nucleotide sequences of the AAV ITR regions for the various AAV serotypes (i.e., AAV-1 to AAV-7) are known in the art and vary in size with the serotpe. Typically, the AAV ITRs range in size from about 125–145 bp. See for example, Kotin, *Human Gene Therapy* 5 (1994) 693–801 and Berns "Parvoviridae and their Replication" in *Fundamental Virology*, 2d Edition (B. N. Fields and D. M. Knipe, eds.). As used here, the AAV ITRs of Applicants' recombinant replication-defective retrovirion need not be identical to the nucleotide sequence of the native, i.e., wild-type, sequence, but may be altered by insertion, deletion or substitution of nucleotides. Further, the two AAV ITRs may be derived from any of the AAV serotypes, for example AAV-1, AAV-2, AAV-3, AAV-4, AAV-5 and AAV-7, and need not be identical to or derived from the same serotype, so long as they permit integration of the heterologous sequence of interest into the recipient cell genome when AAV rep gene products are present in the cell.

The AAV rep coding region is the art-recognized region of the AAV genome that encodes the proteins required for replication of the viral genome and for insertion of the viral genome into a host genome during latent infection. The rep coding region includes at least the four genes encoding the two long forms of rep (rep 78 and rep 68) and the two short forms of rep (rep 52 and rep 40). For more details see, for example, Muzyczka, *Current Topics in Microbiol.* 158 (1992) 97–129 and Kotin, *Human Gene Therapy* 5 (1994) 793-801. The rep coding region may be derived from any AAV serotype or from a functional homologue such as the human herpes virus 6 rep gene. The region need not include all of the native sequence, but may be altered by insertion, deletion or substitution of nucleotides, so long as the sequence that is present provides for sufficient integration when expressed in a suitable recipient cell. Preferably, the AAV vector and virions utilized in the present invention lack one or more of the rep proteins so as to render it replication-defective. More preferably, the AAV vector of the present invention lacks all four of the rep proteins.

The AAV cap coding region is the art-recognized region of the AAV genome that encodes the capsid or coat proteins, VP1, VP2 and VP3, that package the viral genome. For more details, see, for example, Muzyczka, *Current Topics in Microbiol.* 158 (1992) 97–129 and Kotin, *Human Gene Therapy* 5 (1994) 793–801. The cap coding region may be derived from any AAV serotype or from a functional homologue. The cap coding region may be altered by insertion, deletion or substitution of nucleotides, so long as the sequence present provide for sufficient packaging when expressed in a suitable recipient cell. Although the cap coding region is preferably not included in the AAV vectors and the replication-defective AAV virions employed in the present invention, it needs to be included in a helper vector that is expressed in a packaging cell that recognizes and packages the ITRs and the gene(s) positioned therebetween.

Thus, the term "AAV vector", as used herein means a vector derived from an adeno-associated virus serotype that includes at least those sequences required in cis for replication and packaging, for example, a pair of functional ITRs flanking a heterologous (i.e., non-AAV) nucleotide sequence. With this criterion, any AAV vector of any serotype can be employed in the method of this invention. Examples of vectors for use in this invention are the AAV-2 based vectors disclosed in Srivastava, PCT Patent Publication WO 93/09239 or simply a pair of AAV-7 ITRs having one or more genes operatively positioned therebetween.

The AAV ITRs employed in the vectors and virions of the present invention may be the native (wild-type)AAV ITRs or they may be modified. If the ITRs are modified, they are preferably modified at their D-sequences. The native D-sequences of the AAV ITRs are sequences of twenty consecutive nucleotides in each AAV ITR (i.e., there is one sequence at each end) which are not involved in HP formation. The D-sequences of the ITRs are modified by the substitution of nucleotides, such that 5–18 native nucleotides, preferably 10–18 native nucleotides, most preferably 10 native nucleotides, are retained and the remaining nucleotides of the D-sequence are deleted or replaced with non-native, i.e., exogenous, nucleotides. One preferred sequence of five native nucleotides that are retained is 5' CTCCA 3'. The exogenous or non-native replacement nucleotide may be any nucleotide other than the nucleotide found in the native D-sequence at the same position. For example, appropriate replacement nucleotides for native D-sequence nucleotide C are A, T and G, and appropriate replacement nucleotides for. native D-sequence nucleotide A are T, G and C. The construction of four such AAV vectors is disclosed in U.S. Ser. No. 08/921,467, filed Sep. 2, 1997. Other employable exemplary vectors are pWP-19 and pWN-1, both of which are disclosed in Nahreini, *Gene* 124 (1993) 257–62. Another example of such an AAV vector is psub2ol as disclosed in Samulski, *J. Virol.* 61 (1987) 3096.

Other suitable AAV vectors are the Double-D ITR vector. Methods for making the double-D ITR vectors are disclosed in U.S. Pat. No. 5,478,745. Still other suitable AAV vectors are those disclosed in U.S. Pat. No. 4,797,368 (Carter) and U.S. Pat. No. 5,139,941 (Muzyczka), U.S. Pat. No. 5,474,935 (Chartejee) and PCT Patent Publication WO 94/28157 (Kotin). Yet a further example of an AAV vector employable in the methods of this invention is SSV9AFABTKneo, which contains the x-fetoprotein (AFP) enhancer and albumin promoter and directs expression of the herpes simplex thymidine kinase (TK) gene predominantly in the liver. Its structure and method for making are disclosed in Su, *Human Gene Therapy* 7 (1996) 463–70).

The replication-defective AAV vectors are packaged into empty AAV capsids to produce the replication-defective AAV virions helper viruses employed in the methods of the present invention. To package the replication-defective AAV vectors, which are typically one or more genes positioned between a pair of ITRs, one employs a helper construct or helper virus that has AAV-derived coding sequences that function in trans to enable AAV replication, and that include the AAV rep and cap sequences. The helper virus has AAV coding sequences but lacks the AAV ITRs and thus are not packaged in the capsids that are produced. This helper virus then provides for transient expression of the AAV rep and cap genes missing from the AAV vector. For greater details, including exemplary AAV helper constructs, see, for example, Samulski, *J. Virol.* 63 (1989) 3822–28; McCarty, *J. Virol* 65 (1991) 2936–45 and U.S. Pat. No. 5,139,941. One such AAV helper construct comprises pKS rep/cap, which contains the genes encoding the AAV-2 rep and cap polypeptide sequences. Additional examples of helper viruses, constructs and functions that can be employed include the plasmids pAAV/Ad and pIM29+45 (see Samulski, *J. Virol.* 63 (1989) 3822–28 and McCarthy, *J. Virol* 65 (1991) 2936–45) and those disclosed in U.S. Pat. No. 5,622,856.

Accessory functions and accessory function vectors are non-AAV derived functions and vectors containing sequences encoding such functions upon which AAV is dependent for its replication. Such accessory functions can be derived or obtained from any of the known helper viruses, such as adenovirus, herpesvirus (except herpes simplex virus type-1) and vaccinia virus and include moieties and/or sequences involved in activation of gene transcription, DNA replication, synthesis of cap expression products and capsid assembly. See, for example, Carter, "Adeno-Associated Virus Helper Functions" in CRC handbook of Parvoviruses, Vol. I (1990) (P. Tijssen, ed.); Muzyczka, *Current Topics in Microbiol.* 158 (1992) 97–129; Janik, *Proc. Natl. Acad Sci* 78 (1981) 1925–29; Young, *Prog. Med Virol.* 25 (1979) 1213 and Schlehofer, *Virology* 152 (1986) 110–17.

The adenoplasmid accessory constructs employed in the method of the present invention comprise adenovirus plasmid DNA rendered unable to be packaged into adenovirus particles, for example, the adenoplasmid accessory constructs lack the adenovirus packaging signals required for production of infectious adenovirus particles but contain the adenovirus genes required for rAAV virion production. Alternatively, the adenoplasmid accessory construct are rendered to large to be packaged by the additional heterologous sequences, plasmids or other constructs. Use of such adenoplasmid accessory constructs results in the generation of rAAV virions having similar infectious activity and packaging efficiency as compared to prior art methods.

One such construct comprises an adenovirus type 5 plasmid which contains all of the DNA sequence of the serotype 5 adenovirus but lacks the serotype 5 packaging signal which lies between base pairs 194 through 398. See Hearing and Shenk, *Cell* 33 (1983) 695–703; Hearing, *J. Virol.* 61 (1987) 2555–58; Grable and Hearing, *J. Virol.* 64 (1990) 2047–56; Grable and Hearing, *J. Virol.* 64 (1990) 723–31. An alternative construct comprises an adenovirus type 2 plasmid which contains all of the DNA sequence of the serotype 2 adenovirus but lacks the serotype 2 packaging signal, which lies in a similar location. analogously, constructs comprising any other adenovirus serotype may be used, as long as the packaging signal is removed. Exemplary serotypes which can be employed include serotypes Ad1, Ad6, Ad8, Ad9, Ad10, Ad11, Ad12, Ad13, Ad15, Ad17, Ad19, Ad20, Ad22, Ad23, Ad24, Ad25, Ad26, Ad27, Ad28, Ad29, Ad30, Ad32, Ad33, Ad367, Ad37, Ad38, Ad39, Ad40, Ad41 and Ad42. See Fields *Virology*, 2 (Fields and Knipe, eds.), 1990.

Another such construct comprises an adenovirus 5 plasmid which contains heterologous sequences making it too large to be packaged. For example, the insertion of plasmid pBR322 or one of its derivatives at base pair (bp) 1339 (3.7 mu) in the Adenovirus 5 sequence makes the resulting viral genome too large to package. See Bett, *Proc. Natl. Acad. Sci.* 91 (1994) 8802–06 and McGrory, *Virology* 163 (1988) 614–17. An alternative construct comprises an adenovirus type 2 plasmid which contains all of the DNA sequence of the serotype 2 adenovirus but which contains an insertion of pBR322 at a similar location. Analogously, constructs comprising any other adenovirus serotype may be used, as long as the construct is rendered too large to be packaged. Exemplary serotypes which can be employed include Ad1, Ad6, Ad8, Ad9, Ad10, Ad11, Ad12, Ad13, Ad15, Ad17, Ad19, Ad20, Ad22, Ad23, Ad24, Ad25, Ad26, Ad27, Ad28, Ad29, Ad30, Ad32, Ad33, Ad367, Ad37, Ad38, Ad39, Ad40, Ad41 and Ad42. See Fields *Virology*, 2 (Fields and Knipe, eds.), 1990.

The adenoplasmid accessory constructs can alternatively include one or more polynucleotide homologues having substantially identical finctions as the native sequence replacing the native adenoviral sequences. Such homologues may be derived from a different adenovirus serotype (since the nucleotide sequence of the adenovirus type 5 genome is believed to be 99% homologous to the adenovirus type-2 genome), from another accessory virus or from another suitable source.

The adenoplasmid can be in the form of a circularized or linearlized DNA fragment capable of replication when associated with appropriate control elements and which can be transcribed and expressed in a host cell. It can be engineered using conventional recombinant techniques. For example, the adenoplasmid can be assembled by inserting adenovirus nucleotide sequences (either derived from an adenovirus genome, from an adenovirus vector or chemically synthesized) having accessory functions into a vector construct in any desired order, for example, by ligating restriction fragments into the plasmid using polylinker oligonucleotides. The sequences can then be excised from the vector and inserted into an appropriate expression plasmid using techniques well known in the art. One such construct employed in the examples includes plasmid pBHG10, which is a bacterial plasmid that contains the Ad5 sequences required to produce infectious virus upon transfection of 293 cells but lacks the packaging signal, base pairs 194 through 358 needed to encapsidate viral DNA, since it contains a deletion of Ad5 sequences from bp 188 through bp 1339 (0.5 through 3.7 mu). An ampicillin resistance gene and bacterial origin of replication substitute for the deleted Ad5 sequences and the plasmid also lacks the AdS E3 region, from 78.3 through 85.8 map units (mu). Details of its structure and its construction is described in Bett, *Proc. Natl. Acad. Sci.* 91 (1994) 8802–06. It is available from Microbix Biosystems, Inc., Ontario, Canada.

Other adenoplasmid constructs which can be employed include plasmid pBG11, which is non-infectious when transfected into 293 cells, since it contains the same deletion of Ad5 packaging signal sequences as pBHG10 but lacks the Ad5 E3 region from 77.5 through 86.2 mu. Details of its structure and its construction is described in Bett, *Proc. Natl. Acad. Sci.* 91 (1994) 8802–06.

Another exemplary adenoplasmid construct contemplated for use in the invention is pJM17. Construct pjM17 contains an insertion of a derivative of plasmid pBR322 at base pair (bp) 1339 (3.7 mu) in its Adenovirus 5 sequence, which makes the resulting viral genome too large to package. See Bett, *Proc. Natl. Acad. Sci.* 91 (1994) 8802–06 and McGrory, *Virology* 163 (1988) 614–17. The construct pJM17 was derived from pFG140 (see Graham, *EMBO J* 3 (1984) 2917–22), such that vectors generated with pJM17 also contain the same deletion(s) and substitution(s) present in the E3 region of its Ad5 sequence as is present in the vector dl 309 (see Jones, *Cell* 17 (1979) 683–89).

The adenoviral gene regions in the adenoplasmid are operably linked to control sequences that direct their transcription or expression. Such control sequences can comprise the adenoviral control sequences associated with the gene regions of the wild-type adenoviral genes or can comprise heterologous control sequences, such as heterologous promoters derived from mammalian or viral genes. Exemplary heterologous promoters include adenoviral promoters from homologous adenoviruses (i.e., from a different adenoviral serotype), the SV40 early promoter, the mouse mammary tumor virus LRT promoter; the adenovirus major late promoter; a herpes simplex virus promoter, a cytomegalovirus promoter, a rous sarcoma virus promoter, synthetic promoters or hybrid promoters. Such promoters are commercially available.

The adenoplasmid accessory construct can also include one or more selectable markers. Suitable markers are sequences that confer antibiotic resistance or sensitivity, impart color, or change the antigenic character of transfected cells when grown in suitable selective media. Exemplary selectable markers include the hygromycin B resistance gene, the ampicillin resistance gene and the kanamycin resistance gene. Other suitable markers are well known in the art.

Alternatively, suitable host cells may provide one or more of the necessary accessory functions. For example, the human cell line 293 is a human embryonic kidney cell line that has been transformed with adenovirus type 5 DNA fragments so that it expresses adenovirus E1a and E1b genes. Thus, in one embodiment, an adenoplasmid is provided which lacks the packaging signal and the E1a and E1b gene regions. Upon transfection into a 293 hot cell, the adenoplasmid will provide the accessory functions supportive of rAAV virion production, without the formation of infectious adenovirus particles.

The adenoplasmids of the invention can be employed in methods for the production of rAAV virions. One such method entails introducing into a suitable host cell an AAV vector, an AAV helper construct and an adenoplasmid accessory construct into the host cell. The adenoplasmid accessory plasmid is composed of adenovirus plasmid DNA lacking packaging signal sequences as described above. The host cell is cultured to produce crude rAAV virions and lysed. The resulting cell lysate is applied to a chromatographic column or a cesium chloride density gradient and the purified rAAV virions are recovered from the column.

The heterologous nucleotide sequence(s) that are inserted into the replication-defective AAV vectors and virions of the present invention encode one or more therapeutic agents that include a therapeutic protein, polypeptide, antisense RNA or a ribozyme, or a combination thereof. Typically, the vectors or virions contain from one to two therapeutic agents that are native or non-native to the recipient cell but which have a desired biological or therapeutic effect.

As disclosed above, the heterologous nucleotide sequences that are introduced into the replication-defective AAV vectors and virions of the present invention include a gene that encodes a therapeutic protein or polypeptide, preferably a human protein or polypeptide. Examples of therapeutic proteins and polypeptides that would be suitable for expression in the methods of the present invention include the LDL receptor, Factor VIII, Factor IX, phenylalanine hydroxylase, ornithine transcarbamylase, or α1-antitrypsin; a cytokine, such as interleukin (IL)-1, IL-2 IL-3, IL-4, IL-5, IL-6, IL-7, IL-8, IL-9, IL-10, IL-11, IL-12, IL-13, IL-14 and IL-15, α-interferon, β-interferon, the γ-interferons, tumor necrosis factor CD3, ICAM-1, LFA-1, or LFA-3, a chemokine including RANTES 1 $60$ , or MIP-1β(see Cocci, *Science* 70 (1996) 1811–15); a colony stimulating factor, such as G-CSF, GM-CSF and M-CSF; growth factors such as IGF-1 and IGF-2; human hormones such as growth hormone, insulin, calcitonin, prolactin, follicle stimulating hormone, luteinizing hormone, chorionic gonadotropin or thyroid stimulating hormone; any one of the hepatitis genes; thrombopoietin, erythropoietin, or leptin or a combination of the above. The nucleotide coding sequences for these proteins and polypeptides are already known in the art. Even more sequences expressible in the methods and compositions of the invention include Protein S and Gas6, thrombin, Coagulation Factor Xa, acidic fibroblast growth factor (FGF-1), basic FGF (FGF-2), keratinocyte growth factor (KGF), TGF, platelet derived growth factor (PDGF), epidermal growth factor (EGF), hepatocyte growth factor (HGF) and HGF activators, PSA, nerve cell growth factor (NCGF), glial cell derived nerve growth factor (GDNF), vascular endothelial growth factor (VEGF), Arg-vasopressin, thyroid hormones asoxymethane, triodothyronine, LIF, amphiregulin, soluble thrombomodulin, stem cell factor, osteogenic protein 1, the bone morphogenic proteins, MFG, MGSA, heregulins and melanotropin. Preferred proteins include but are not limited to erythropoietin, thrombopoietin (G-CSF), Factor VIII, Factor IX, Factor Xa, human growth hormone, leptin and IL-2, the DNA sequences of which are all known in the art, particularly the human DNA sequences.

The AAV vector may also include control sequences, such as promoters and polyadenylation sites, selectable markers, reporter genes, enhancers and other control elements permitting for transcription induction and/or selection. Such AAV vectors can be constructed using techniques well known in the art.

The replication-defective AAV helper construct is used to complement the AAV vector by providing those genes, which are necessary for the production of AAV virions, particularly the cap structural genes. Suitable helper constructs having complementing functions are well known in the art.

The AAV vector, the replication-defective AAV helper construct and adenoplasmid accessory construct are introduced into the host cell either simultaneously or sequentially, using any of the well known, art recognized transfection techniques, for example, by calcium phosphate co-precipitation. Culture conditions include incubating in the range of 35°–40° C. for approximately 48 to 120 hours. The cells are collected and a lysate produced using three freeze/thaw cycles and/or sonication. The lysates are then centrifuged to remove cell debris and the rAAV virions purified by cesium chloride equilibrium gradient centrifugation. Any residual adenoviral particles are inactivated by heating the purified rAAV preparation to at least 56° C. for 20–30 minutes. Alternatively, the rAAV virions can be purified by sulfonated cellulose column chromatography following the protocol described in Tamayose, *Human Gene Therapy* 7 (1996) 507–513.

Examples of the above provided description are provided below.

EXAMPLE 1

Construction of AAV Vector pCMVAAV-IacZ, Helper Plasmid PKSrep/cap and Adenovirus Plasmids pJM17, pBHG10 and pBHG11

Vector pKm 201 CMV is a cloning vector in which an expression cassette containing a CMV immediate early enhancer, promoter and intron and a bovine growth hormone poly adenylation site is flanked by AAV-2 ITRs. pKm 201 CMV was derived from pKm201, a modified AAV vector plasmid in which the ampicillin resistance gene of pEMBL-AAV-ITR (Srivastava, (1989)) has been replaced with the gene for kanamycin resistance. The expression cassette from pCMVlink, a derivative of pCMV6c (Chapman, (1991), in which the bGH poly A site has been substituted for the SV40 termination site, was inserted between the ITRs of pKm201to generate pKm201CMVLINK. To construct pCMVAAV-lacZ, the lacZ cDNA sequence was excised from the plasmid pCMVβ, (Clontech, Palo Alto, Calif.) and inserted into pKm201CMVLINK. The plasmid pKm201CMVLINK has the backbone identical to vector pAAV-TK-MCSFa, which has been deposited with the ATCC, as Accession No. 98335.

The AAV helper plasmid, pKSreplcap was constructed by cloning the AAV-2 genome without the ITRs, i.e., nucleotides 192 through 4493 of AAV-2 (see Srivastava, *J. Virol.* 45 (1983) 555–64) into pBluescript II KS+(Strategene, La Jolla, Calif.).

Adenovirus plasmids pJM17, pBHG10 and pBHG11are described in Bett, *Proc. Natl. Acad. Sci.* 91 (1994) 8802–06. Plasmid pJM17 is a non-infectious (replication-defective) adenovirus plasmid when transfected into human embryonic kidney cells (293 cells), since it contains an insertion of a derivative of plasmid pBR322 at base pair (bp) 1339 (3.7 mu) in its Adenovirus-5 sequence, which makes the resulting viral genome too large to package. Plasmid pBHG10 is an Adenovirus-5 plasmid that is non-infectious when transfected into 293 cells, since it contains a deletion of Adenovirus type 5 (Ad5) sequences from bp 188 through bp 1339 (0.5 through 3.7 mu), which removes the packaging signals (psi) required to encapsidate the adenoviral DNA. An ampicillin resistance gene (Ap) and bacterial origin of replication (Ori) substitute for the deleted (bp 188 to 1339) Ad5 sequences. This plasmid also lacks the Ad5 E3 region (from 78.3 through 85.8 mu). Plasmid pBHG 11 is an Ad5 plasmid that is infectious when transfected into 293 cells, since it contains a deletion of Ad5 sequences from bp 188 through bp 1339 (0.5 through 3.7 mu) which removes the packaging signals (psi) required to encapsidate the adenoviral DNA. An ampicillin resistance gene (Amp$^r$) and bacterial origin of replication (Ori) substitute for the deleted Ad5 sequences. This plasmid also lacks the Ad5E3 region (from 77.5 through 86.2 mu).

EXAMPLE 2

Generation of rAAV Particles by Triple Transfection

For generation of replication defective rAAV particles (virions) by the triple transfection method of the present invention, the transient plasmid transfection protocol disclosed in Zhou (1994) was followed with minor modifications. Human embryonic kidney cells (293 cells) available from the ATCC under Accession No. CRL1573 (see also, Graham, *J. Gen. Virol.* 36 (date) 59–72) were grown in sterile IMDM medium (Biowhittaker, Mass.) containing 10% fetal bovine serum at 37° C. in 5% $CO_2$. Once the cells had reached 60–70% confluency on a 15 cm dish, the cells were triple transfected with a mixture comprising the AAV vector, the replication-defective AAV helper plasmid and the adenoviral plasmid by the calcium phosphate co-precipitation method. In particular, a mixture of 10 µg of the AAV vector plasmid, 10µg of the replication-defective AAV helper plasmid and 20 µg of the adenoplasmid pBHG10 was added to 2.5 ml of 250 mM $CaCl_2$ and mixed with 2.5 ml of 2x HBS (Jordan, *Nucleic Acids. Res.* 24 (1996) 596–601). The precipitate was left on the cells for eight hours and replaced with fresh IMDM medium containing 10% fetal bovine serum (FBS). At 24, 48, 72, 96 and 120 hours after transfection, the cells were harvested with Hepes buffer (2.5 ml/dish) and lysed by three cycles of freezing and thawing. The cell lysates were centrifuged at 12,000x g for twenty minutes to remove cell debris. The packaged AAV particles were purified through two rounds of cesium chloride equilibrium gradient centrifugation and residual adenoviral particles were inactivated by heat treatment at 56° C. for thirty minutes. Alternatively, the packaged AAV particles are purified by sulfonated cellulose column chromatography as described in Tamayose, *Human Gene Therapy* 7 (1996) 507–13.

Another set of transfections involved an identical protocol, except that the adenoplasmid DNA was not used; instead, eight hours post transfection the cells were infected with adenovirus dl 312 at a multiplicity of infection (MOI) of 2. Adenovirus dl 312 has a deletion in the E1a gene and is propagated in 293 cells transformed with left-end of adenovirus sequences. It expresses E1a and E1b transcripts. See Moran *Cell* 48 (1987) 177–78. The transformed cells were harvested at 72 hours post-infection and purified as described above.

For estimation of the total number of vector particles produced, the purified vector stock was treated with DNAse I and the encapsidated DNA was extracted with phenol-chloroform, precipitated with ethanol, and subject to dot blot analysis as described in Nahreini and Srivastava, *Interviriology* 30 (1989) 74–85. 293 cells were then infected with serial dilutions of vector stock. The positive cells were counted and the functional titer was estimated. For wild-type AAV testing, the rAAV stock was diluted serially and 293 cells ($2 \times 10^5$) were infected along with Ad at an MOI of 2. Three days later the cells were harvested, lysed by three freeze/thaw cycles and the cell debris removed by centrifugation. The supernatant was heat-inactivated for ten minutes and fresh 293 cells ($6 \times 10^6$) were infected in the presence of Ad at an MOI of 2. At 48 hours post-infection, the low molecular weight DNA was isolated following the method of Hirt, *J. Mol. Biol.* 26 (1967) 365–69, fractionated on an agarose gel and transferred to a nylon membrane. The blot was hybridyzed to a biotinylated oligonucleotide probe specific for the AAV capsid region. The titer was reported base on the highest dilution of the vector stock showing positive signal for AAV capsid DNA.

To visualize the amount of adeno- and AAV protein in the preparations by Western blot analysis, aliquots from the crude lysate and final preparation (5 µl (0.008% of the total) of the freeze/thaw lysate and 5 µl (0.5% of the total) of the final products) were electrophoresed on 10% Tris-Glycine gels (Novex, San Diego, Calif.) and electroblotted onto nitrocellulose. The blots were probed with either a monoclonal antibody against AAV capsid protein (ARP Inc., Belmont, Mass.) and a goat anti-mouse (IgG HRP conjugate (Bo-Rad Laboratories, Richmond, Calif.) or a polyclonal antibody against adenovirus type 5 (DAKO, Denmark) and a goat anti-rabbit IgG HRP conjugate. The signal was detected using a chemiluminescence detection kit (ECTL, Amersham, Bukinghamshire, Great Britain).

The results of the Western blot analysis of adenovirus proteins are as follows. Lane 1, which contained the crude preparation (0.008% of the total) from the standard protocol, showed an extensive smear of protein extending from about 29 kD to over 140 kD. Under similar testing conditions, lane 2, which contained the crude preparation (0.008%) from the triple transfection protocol, showed very low levels of adenoproteins. The purified AAV products, when analyzed for adenovirus protein contamination, showed still some adenoprotein contamination in standard protocol (lane 3), whereas the triple transfection protocol of the present invention had no detectable adenoprotein contamination (lane 4). For adenovirus contamination testing, the samples were diluted and added to 50% confluent 293 cells (plated on 12 well dishes with $1 \times 10^5$ cells). The cultures were passaged for at least three weeks or until the cultures exhibited cytopathic effect. The Control included 293 cells infected with known amount of adenovirus stock. The limit of detection in the assay was 100 pfu/ml. These results demonstrated that the triple transfection protocol does not lead to adenovirus contamination.

To determine whether using a replication-defective adenoplasmid accessory construct in place of a replication-competent (helper) adenovirus inhibited AAV virion production, we compared the number of "total" and "functional" rAAV virions obtained from freeze/thaw lysates/10 cm culture dish for the standard protocol of the prior art and the triple transfection protocol of the present invention. Total particles were determined by dot blot analysis. Functional particles were determined by staining for X-gal activity and counting positive cells.

TABLE 1

Comparison of Time Course of rAAV Production By Standard Versus Triple Transfection Protocols

|  | Total Particles | Functional Particles |
|---|---|---|
| Stanadrd Protocol |  |  |
| 72 hours | $4.5 \times 10^{11}$ | $1 \times 10^9$ |
| Triple Transfection Protocol |  |  |
| 24 hours | $1.6 \times 10^{11}$ | $3.2 \times 10^7$ |
| 48 hours | $6 \times 10^{11}$ | $6.6 \times 10^8$ |
| 72 hours | $7 \times 10^{11}$ | $7.4 \times 10^8$ |
| 96 hours | $7 \times 10^{11}$ | $1.5 \times 10^8$ |
| 120 hours | $9 \times 10^{11}$ | $8.6 \times 10^7$ |

The data from Table 1 demonstrate that even in the absence of a productive (replication-competent) adenovirus infection, the encapsidation of rAAV particles is efficiently obtained in human 293 cells provided with adenoviral DNA from an adenoplasmid accessory construct. This experiment also demonstrates that cells transformed with adenoplasmid accessory element had similar numbers of total viral particles between 72–120 hours, and that at 72 hours, the total numbers of particles generated by both methods was comparable and the cell numbers per dish were similar.

EXAMPLE 3

Scale Up Of The Triple Transfection Method

Large-scale transfections were performed as described in Example 2. Replication-defective AAV particles (virions) encoding a gene of interest but free of coding sequences for AAV proteins, were recovered from twenty 15 cm dishes and purified on a CsCl gradient. Total particles and functional particles were estimated as described in Example 2. The results are shown below.

TABLE 2

Comparison of Purified rAAV Particles Generated By Standard Versus Triple Transfection Protocol

|  | Total Particles | | Functional Particles | |
|---|---|---|---|---|
| Method | Lysate | Purified Stock | Lysate | Purified Stock |
| Standard | $6 \times 10^{13}$ | $1.5 \times 10^{13}$ | $6.4 \times 10^{10}$ | $3.9 \times 10^{10}$ |
| Triple Transfection | $5.1 \times 10^{13}$ | $1.3 \times 10^{13}$ | $7.6 \times 10^{10}$ | $3.4 \times 10^{10}$ |

After CsCl gradient purification, adenoviral protein contamination was undetectable by Western blot technique in rAAV preparations prepared by the triple transfection protocol.

All patents, patent publications, patent applications and scientific articles mentioned in this specification are herein incorporated by reference. The invention now being fully described, it will be apparent to one of ordinary skill in the art that many changes and modifications can be make thereto without departing from the spirit or scope of the appended claims.

What is claim is:

1. A method for producing replication-defective recombinant AAV virions substantially free of wild-type AAV and helper adenovirus, comprising:

a. introducing into a suitable host cell (i) an AAV vector that is free of AAV coding sequences and that comprises a heterologous gene operatively positioned between two AAV ITRs, (ii) an AAV helper construct having at least one gene encoding an AAV capsid protein, and (iii) an adenoplasmid accessory construct having a full adenoviral genome that either lacks a packaging signal or that contains sufficient additional nucleotides to be rendered unpackagable, to produce a transformed host cell;

b. culturing the transformed host cell to produce replication-defective recombinant AAV virions having said heterologous gene; and c. lysing the cultured host cell to obtain said replication-defective recombinant AAV virions substantially free of wild-type AAV and adenovirus particles.

2. The method of claim 1, wherein the adenoplasmid accessory construct has a full adenoviral genome that lacks a packaging signal.

3. The method of claim 1, wherein the adenoplasmid accessory construct having a full adenoviral genome that contains sufficient additional nucleotides to be rendered unpackagable.

4. The method of claim 1, wherein the heterologous gene encodes a human protein.

5. The method of claim 4, wherein said human protein is erythropojetin, thrombopoietin (G-CSF), Factor VIII, Factor IX, Factor Xa, human growth hormone, leptin or IL-2.

6. The method of claim 1, wherein the adenoplasmid accessory construct is pJM 17, PBHG 10 or PBHG 11.

7. The method of claim 1 further comprising the steps of:

d. applying the lysate of step (c) to a column comprising sulfonated cellulose; and e. recovering purified replication-defective recombinant AAV virions substantially free of host cell proteins and host cell debris.

8. The method of claim 2, wherein the heterologous gene encodes a human protein.

9. The method of claim 8, wherein said human protein is erythropoietin, thrombopoietin (G-CSF), Factor VIII, Factor IX, Factor Xa, human growth hormone, leptin or IL-2.

10. The method of claim 2, wherein the adenoplasmid accessory construct is pJM17, pBHG10or pBHG11.

11. The method of claim 2 further comprising the steps of:

d. applying the lysate of step (c) to a column comprising sulfonated cellulose; and e. recovering purified replication-defective recombinant AAV rions substantially free of host cell proteins and host cell debris.

12. The method of claim 3, wherein the heterologous gene encodes a human protein.

13. The method of claim 12, wherein said human protein is erythropoietin, thrombopoietin (G-CSF), Factor VIII, Factor IX, Factor Xa, human growth hormone, leptin or IL-2.

14. The method of claim 3, wherein the adenoplasmid accessory construct is pJM17, pBHG10 or pBHG 11.

15. The method of claim 3 further comprising the steps of:

d. applying the lysate of step (c) to a column comprising sulfonated cellulose; and e. recovering purified replication-defective recombinant AAV virions substantially free of host cell proteins and host cell debris.

16. The method of claim 1, wherein in said two AAV ITRs are wild-type.

17. The method of claim 16, wherein said two AAV ITRs are AAV-2 ITRs.

* * * * *